US006928137B2

(12) United States Patent
Bruder et al.

(10) Patent No.: US 6,928,137 B2
(45) Date of Patent: Aug. 9, 2005

(54) METHOD FOR GENERATING AN IMAGE BY MEANS OF A TOMOGRAPHY CAPABLE X-RAY DEVICE WITH MULTI-ROW X-RAY DETECTOR ARRAY

(75) Inventors: Herbert Bruder, Hoechstadt (DE); Thomas Flohr, Uehlfeld (DE); Karl Stierstorfer, Erlangen (DE); Kwok Tam, Edison, NJ (US)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 10/671,894

(22) Filed: Sep. 26, 2003

(65) Prior Publication Data

US 2004/0141581 A1 Jul. 22, 2004

(Under 37 CFR 1.47)

(30) Foreign Application Priority Data

Sep. 27, 2002 (DE) .......................................... 102 45 116

(51) Int. Cl.[7] ............................................ G01N 23/083
(52) U.S. Cl. .......................................................... 378/4
(58) Field of Search ........................................ 378/4–20

(56) References Cited

U.S. PATENT DOCUMENTS

| 4,174,481 A | * | 11/1979 | Liebetruth | .................... | 378/20 |
| 5,170,439 A | | 12/1992 | Zeng et al. | | |
| 5,270,926 A | | 12/1993 | Tam | | |
| 5,315,628 A | | 5/1994 | Guendel | | |
| 5,784,481 A | * | 7/1998 | Hu | .............................. | 382/131 |
| 5,946,370 A | * | 8/1999 | Adler et al. | .................... | 378/4 |
| 6,014,419 A | | 1/2000 | Hu | | |
| 6,028,907 A | * | 2/2000 | Adler et al. | .................... | 378/4 |
| 6,173,033 B1 | | 1/2001 | Klingenbeck-Regn et al. | | |
| 6,504,892 B1 | * | 1/2003 | Ning | .............................. | 378/4 |

OTHER PUBLICATIONS

"Advanced Single–Slice Rebinning In Cone–Beam Spiral CT," Kacheltriess et al, Med. Phys. vol. 27, No. 4 (2000) pp. 754–772.
"Novel Approximate Approach For High–Quality Image Reconstruction in Helical Cone Beam CT At Arbitrary Pitch," Schaller et al, SPIE Med. Imag. Conf., vol. 4322 (2001), pp. 113–127.
"Exact Radon Rebinning Algorithm for the Long Object Problem in Helical Cone–Beam CT," Schaller et al, IEEE Trans. On Medical Imaging, vol. 19, No. 5 (May 2000) pp. 361–375.

(Continued)

Primary Examiner—Edward J. Glick
Assistant Examiner—Thomas R. Artman
(74) Attorney, Agent, or Firm—Schiff Hardin LLP

(57) ABSTRACT

In a method for generating an image of an examination subject with a tomography-capable X-ray device, particularly a computed tomography device, having a multi-row X-ray detector array, an X-ray radiator that rotates about a system axis and emits a conical x-ray beam, and a positioning device by means of which the subject is positionable relative to the X-ray radiator in different z-positions in a direction parallel to the system axis, the image is reconstructed from the raw data that are generated from the X-ray radiator. Raw data are generated from both a rotation scan and a linear scan. In the linear scan, all transmission values for the image reconstruction are acquired in one continuous linear scanning movement, so that the rotation scan can be picked up while the X-ray radiator is in continuous rotation. A topogram that is executed prior to the actual rotation scan for the purpose of selecting a region of interest of the subject for the subsequent rotation scan can be utilized as a linear measurement dataset. A particularly rapid acquisition of initial data for the subsequent 3D image reconstruction occurs.

8 Claims, 3 Drawing Sheets

OTHER PUBLICATIONS

Cone–Beam Filteredj–Backprojection Algorithm For Truncated Helical Data, Kud et al, Phys. Med. Biol., vol. 43 (1998) pp. 2885–2909.

"An Inversion Formula For Cone–Beam Reconstruction," Tuy, Siam J. on App. Mathematics, vol. 43, No. 3 (1983) pp. 546–552.

"A Cone–Beam Tomography Algorithm for Orthogonal Circle–and–Line Orbit," Zeng et al, Phys. Med. Biol., vol. 37, No. 3 (1992) pp. 563–577.

"Digitale Detektorsysteme für die Projektionsradiographie," Schulz, Fortschritte auf Dem Gebiel der Röntgenstrahlen und der Bildgebenden Verfahren, vol. 173 (2001) pp. 1137–1146.

* cited by examiner

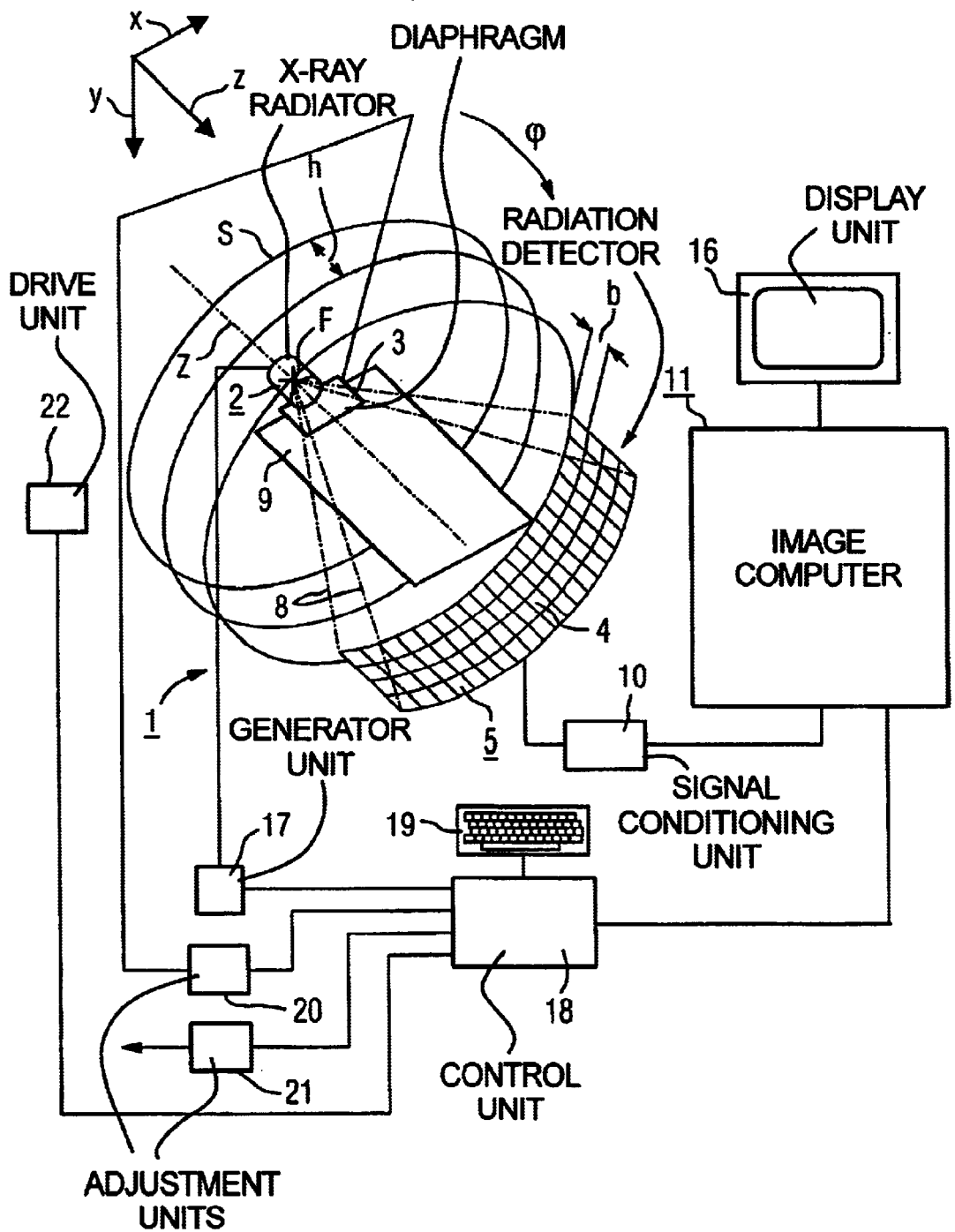

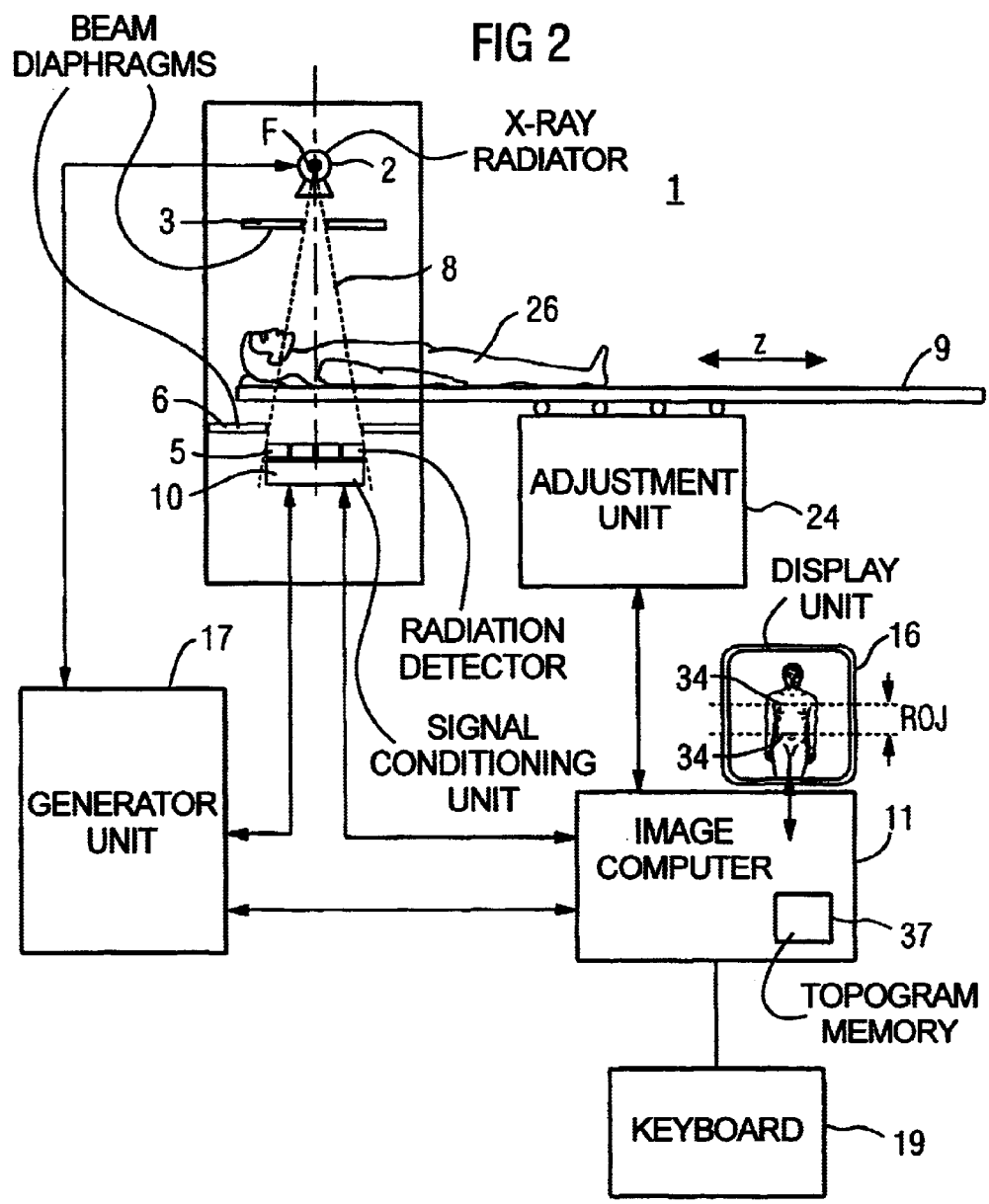

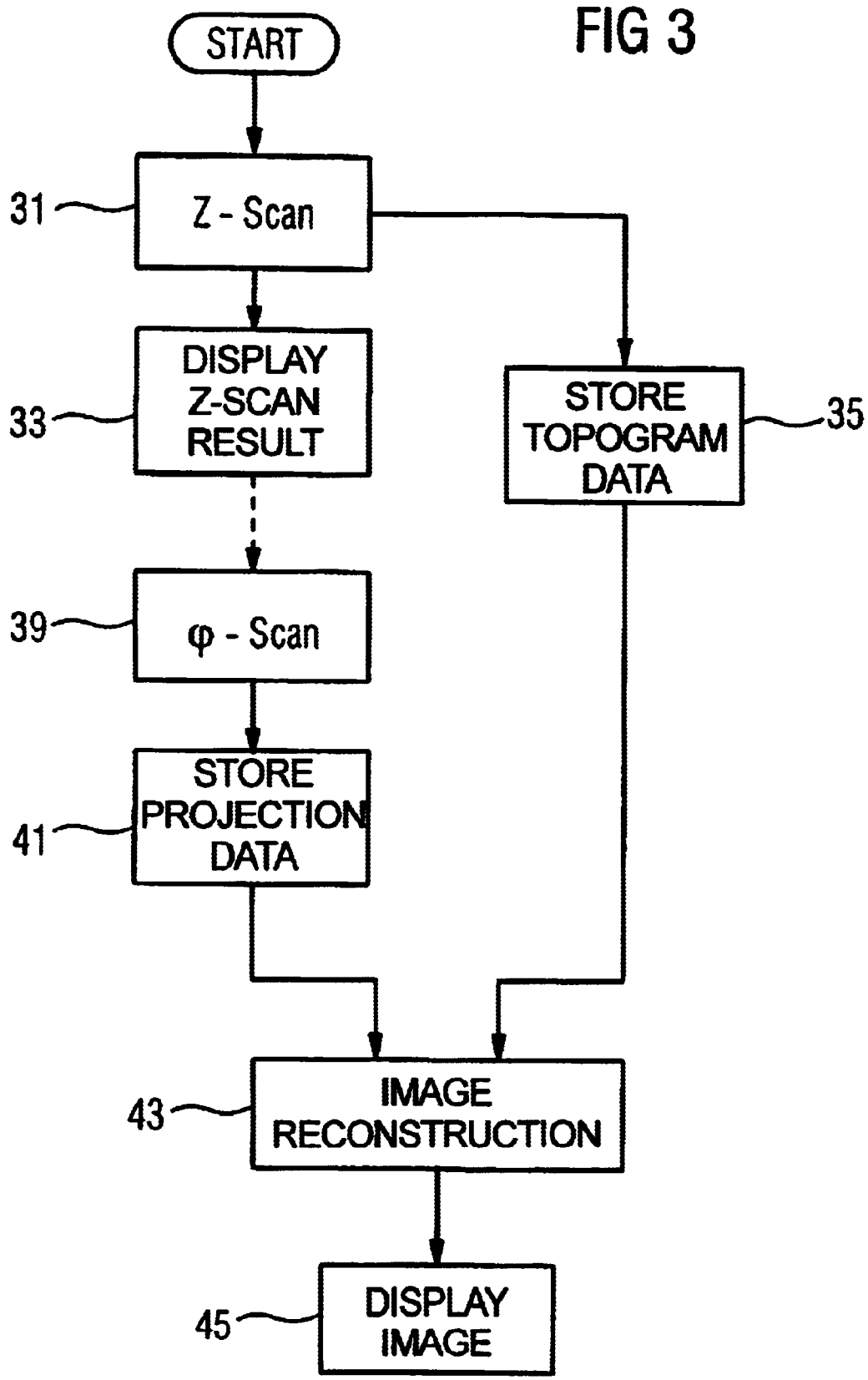

METHOD FOR GENERATING AN IMAGE BY MEANS OF A TOMOGRAPHY CAPABLE X-RAY DEVICE WITH MULTI-ROW X-RAY DETECTOR ARRAY

BACKGROUND OF THE INVENTION

1. Field of the Invention

The present invention relates to a method for generating an image of an examination subject with a tomography-capable X-ray device, particularly with An X-ray computed tomography device, having a multi-row X-ray detector array, an X-ray radiator that rotates around a system axis and emits a conical X-ray beam, and a positioning device by allowing an examination subject to be positioned in a direction parallel to the system axis at various z-positions relative to the X-ray radiator.

2. Description of the Prior Art

In two-dimensional computed tomography, raw data are acquired for subsequent image reconstruction by means of fan beam devices, for example. A fan beam device of this type has a single detector row with individual detector elements disposed in the azimuthal direction. In conformance with this detector geometry, a planar X-ray fan is generated by means of a gating (diaphragm) device. While the X-ray radiator rotates, a number of different projections of the examination subject, namely the patient, are acquired. If the relative distance between the X-ray radiator and the examination subject in a direction parallel to the system axis remains unchanged during this rotation, a single slice, i.e., a two-dimensional portion, of the examination subject is scanned. The result of a subsequent image reconstruction employing algorithms known as convolution algorithms (filtered back projection) is then a two-dimensional topogram or CT image of the scanned slice perpendicular to the rotational axis or system axis.

For the purpose of scanning a volume of the examination subject, raw data of a respective slice are generated in succession at different relative positions (z-positions) of the X-ray radiator relative to the examination subject along a direction parallel to the system axis in a sequence scan, and for each slice a two-dimensional image reconstruction is performed. The tomograms that result from the individual image reconstructions can then be assembled into a 3D image in a stacked fashion.

Overview exposures or topograms are a known means of locating a desired slice or a desired volume in a subject or patient that is to be scanned in the z-direction. For this projection technique, the scanning system remains in a fixed angle position, e.g. X-ray tube and detector above and below the patient. The patient is then moved through the measuring opening. The resulting row attenuation profiles are assembled into a shadow image in the computer and displayed on an image monitor. The desired imaging or scan region can then be selected using marks that can be mixed in, and the positioning of the system components necessary to scan this region can automatically occur. Suitable methods and devices for this are known from German PS 42 23 430 and German PS 197 21 535, for example.

Spiral scanning, wherein the X-ray radiator travels along a helical path around the subject with continuous motion along the system axis, was developed specifically for improving the image contrast. Spiral scanning also can be performed by means of the above-mentioned 2D reconstruction technique by the initial determination of planar datasets (using procedures known as spiral algorithms or slice interpolation processes) from the data that arise during the spiral scan, in a preliminary step prior to the actual image reconstruction.

Computed tomography devices with multi-row X-ray detector arrays have been recently developed. The advantages of these devices are better image contrast, smaller radiation dose for the patient, and shorter examination time, as well as a reduction of movement artifacts associated with movements of the patient during examination (e.g. heart exam). The gating of the X-ray beam onto such a multi-row X-ray detector is no longer two-dimensional as in a fan beam device, but instead is three-dimensional, hence the term conical beam devices (Cone Beam CT Scanner). Due to the cone-shaped scan, a correction of the oblique beam path in the volume is generally required. This requires special 3D reconstruction methods, known as cone beam image reconstruction methods. A distinction is made between approximative methods and exact methods.

Approximative algorithms, for instance algorithms based on a 2D Radon inversion, are described in the article "Advanced Single-Slice Rebinning in Cone-Beam Spiral CT" (M. Kachelriess, S. Schaller, W. A. Kalender; Med Phys. Vol. 27, 4 (2000): 745–772) and in the article "Novel Approximate Approach For High-Quality Image Reconstruction In Helical Cone Beam CT At Arbitrary Pitch" (S. Schaller, K. Stierstorfer, H. Bruder, M. Kachelriess, T. Flohr, SPIE Med. Imag. Conf., V. 4322 (2001): 113–127. These algorithms are highly flexible, for instance with respect to the free adjustability of the pitch (ratio of z shift per rotation to slice thickness); however, they are not sufficiently precise in detector arrays having a larger number of rows, for instance more than four rows, because the error emerging from the approximation grows as the cone angle increases.

Therefore, methods also have been developed which precisely account for the cone angle. The article "Exact Radon Rebinning Algorithm For The Long Object Problem In Helical Cone-Beam CT" (S. Schaller, F. Noo, F. Sauer, K. C. Tam, G. Lauritsch, T. Flohr; Proc. of the 1999 Int. Meeting on Fully 3D Image Reconstruction (1999): 11–14) and the article Cone-Beam Filtered-Backprojection Algorithm For Truncated Helical Data (H. Kudo, F. Noo, M. Defrise; Phys. Med. Biol., v. 43 (1998): 2885–2909) describe such methods for flat detectors with a large number of rows, e.g. 256 rows, and with a large cone spread. These exact cone beam algorithms, however, require a maximal table displacement of approximately 1.5 times the detector height for optimum use of the detector data and the applied dose. Such high displacement speed is undesirable in many instances.

In order to determine a complete dataset that is sufficient for a 3D reconstruction, a criterion known as Tuy's condition must be satisfied, as describe& in "An Inversion Formula For Cone Beam Reconstruction" (H. Tuy, SIAM Journal on Applied Mathematics, v. 43, Nr. 3 (1983): 546–552. According to this condition, each plane through the image subject must be intersected by the path of the X-ray focus at least once. The dataset that is generated in a rotation scan such as a sequence scan alone is therefore insufficient for a 3D reconstruction. In other words, the scan in the 3D Radon space is incomplete. Ideally, this should contain all planar integrals of the beam cone of planes oriented randomly in the examination subject, as is mathematically expressed by Equation (15) of the Tuy article.

In order to obtain a complete dataset (data record) for a cone beam image reconstruction process, according to U.S. Pat. Nos. 6,014,419 and 5,170,439, the rotation scan is combined with a linear scan, and the total data volume is used as the starting dataset for the image reconstruction. According to the cited references, a combination of a linear scan and a rotational scan takes place multiple times in succession until the relevant volume has been scanned completely. In this "circle and line orbit," the rotation of the X-ray radiator must be interrupted after each step of the rotation scan in order to be able to execute one of the many linear scan steps while the radiator is not rotating. As described in U.S. Pat. No. 6,014,419, this constant interrupting of the rotational movement is undesirable and creates a time disadvantage. This reference therefore proposes an alternative, known as a "circle and helix scan," which is intended to reduce the overall data acquisition time substantially.

SUMMARY OF THE INVENTION

An object of the present invention is to provide a method for generating an image of an examination subject with a computer tomography device, wherein the initial data (starting dataset) for a subsequent image reconstruction can be acquired in an even shorter time.

This object cited at the outset, is achieved in a first embodiment of the invention in a method of the type initially described, and wherein a rotation scan and a linear scan are employed to generate the image data, and wherein all transmission (attenuation) values for the image reconstruction that are generated by the linear scan are acquired in one continuous linear scanning movement. The totality of all-linear scan values that are needed for a complete 3D image reconstruction thus are acquired in a unified common scanning step. Thus, the data required for an image reconstruction can be generated particularly rapidly. The transmission values that are obtained from the linear scan, in particular, serve for expanding the projection data that are obtained from the rotation scan in consideration of Tuy's condition. The data from the rotational scan (circle scan) and the linear scan (line scan) arise at least partly from the same measurement volume of the subject.

In the inventive method, a tomography-capable X-ray device, namely an X-ray diagnostic system, is used, by means of which an image reconstruction can be executed from a multiple sets of transmission data that are picked up at various angles and combined into a raw dataset. These devices can be realized mechanically either as a computed tomography device or in the form of a C-arm device.

In a computed tomography device, an X-ray radiator, and generally the allocated X-ray detector rotate in full revolutions around the patient axis. The desired anatomical volume is scanned by incremental displacement (sequence mode) of the patient support table relative to the X-ray radiator and detector, or alternatively by continuous table displacement (spiral scan). In a C-arm device, only partial revolutions of less than 360° are possible, but this can be sufficient for an image reconstruction.

According to the inventive method, the CT image or topogram is reconstructed on the basis of a pure 3D reconstruction algorithm.

According to the inventive method, the image reconstruction can be carried out by means of different techniques. The cone beam reconstruction methods described in U.S. Pat. No. 5,270,926 or in the article "A Cone Beam Tomography Algorithm For Orthogonal Circle-And-Line Orbit" (G. L. Zeng, G. T. Gullberg, Phys. Med. Biol., v. 37. no. 3 (1992): 563–577) are examples.

The cone-shaped beam may also be referred to as a cone beam.

According to the inventive method, the transmission values are picked up in immediate succession during the continuous linear scanning motion, without any intermediate rotation of the X-ray radiator. It is therefore unnecessary to accelerate the rotating gantry to full rotation speed after the end of a line scan and decelerate it into a resting state before the beginning of a line scan, as is necessary in conventional "circle and line orbit" techniques.

In corresponding fashion, all projections for image reconstruction that are generated by rotational scanning are picked up in one continuous rotational movement of the X-ray radiator. The advantage of this is that constant braking and accelerating, and the associated inertia forces, can be eliminated. The X-ray radiator can perform a spiral scan during the rotational scanning step, for example.

It is particularly advantageous, however, for the rotation scan according to the inventive to proceed at settings of different z-positions in succession and to acquire multiple projections at the same z-position during at least one revolution of the X-ray radiator around the subject. For instance, a number of planes situated perpendicular to the system axis or rotational axis are successively scanned (sequence scan).

In the first embodiment, the X-ray detector preferably is a flat detector, i.e., an X-ray detector having at least 64, preferably 256 detector rows: In the rotation scan, a number of projections are acquired at a single z-position during at least one revolution of the X-ray radiator around the subject. This type of operating mode is particularly appropriate for dynamic examinations of hearts, particularly if the flat detector is able to acquire the entire heart volume in the z-direction without changing the z-position. Multiple revolutions in combination with retrospective data sorting then make possible exact display of the heart phases in high time resolution.

The versions directed to a sequence operating mode, wherein a number of projections are acquired at one or more constant z-positions, are based on the consideration that the abovementioned precise cone beam reconstruction algorithms that have been developed for spiral mode generally require a large table displacement, which is undesirable for many instances, particularly in the field of dynamic examination of the heart. With the inventive method, examination in a sequence mode is possible, while sufficient data are nevertheless generated for a 3D image reconstruction.

In a preferred version of the first embodiment, the linear scan is conducted as a topogram. In an examination with a computed tomography device, such a topogram, also referred to as a shadow image or overview exposure, generally is obtained by medical personnel anyway before the beginning of the diagnostic examination in order to localize the relevant region. In the preferred version of the first embodiment of the method, the topogram data that are acquired in any case prior to the actual CT measurement, which conventionally have served simply for orienting the patient, are used in the image reconstruction.

In a second embodiment of the invention, the aforementioned object is achieved in a method of the type initially described wherein a topogram is picked up by registering transmission values at different z-positions of a subject without rotation of the X-ray radiator, the topogram is displayed on a display unit for the purpose of selecting a relevant region of the subject, the topogram is stored, a rotation scan is performed, in which a number of projections are picked up during at least one revolution or partial revolution of the X-ray radiator around the subject, and the image is reconstructed from the stored topogram data in combination with the raw data that are picked up during the rotation scan.

The descriptions, advantages, and preferred embodiments set forth above in connection with the first embodiment of the inventive method apply in analogous fashion to the second embodiment.

As in the first embodiment, when a flat detector is used in the second embodiment, the topogram is picked up with the entire active recognition surface thereof.

The rotation scan covers at least the relevant region. Thus, in the extreme case, one rotation scan is sufficient.

In a particularly version of the second embodiment, all projections for the image reconstruction that are generated by rotation scanning are picked up in one continuous rotational movement of the X-ray radiator.

DESCRIPTION OF THE DRAWINGS

FIG. 1 is a block diagram of a computed tomography in a simplified perspective view that is operable in accordance with the inventive method.

FIG. 2: is a side sectional view of a computed tomography apparatus similar to the apparatus of FIG. 1.

FIG. 3 is a flowchart of an exemplary embodiment of the inventive method.

DESCRIPTION OF THE PREFERRED EMBODIMENTS

FIG. 1 illustrates a third generation CT device 1 that is operable in accordance with the invention. Its measuring arrangement has an X-ray radiator 2 with a radiation diaphragm 3 in the beam path and an X-ray detector 5 that is constructed as a flat array of several rows and columns of detector elements (one of which is referenced 4 in FIG. 1) with an optional beam diaphragm 6 (see FIG. 2) in front of it in the beam path. For simplification, only four rows of detector elements 4 are shown in FIG. 1, but the two-dimensional detector 5 has additional rows of detector elements 4, optionally with different widths b. The X-ray detector 5 is constructed as a solid-state matrix detector system, particularly a flat image detector and/or a scintillator layer, preferably an unstructured layer, with an allocated electronic photo receiver matrix, for instance a-Si based. This type of a-Si detector is described in the article "Digitale Detektorsysteme für die Projektionsradiographie" (R. F. Schulz, Fortschritte auf dem Gebiet der Roentgenstrahlen und der bildgebenden Verfahren (Röfo), v, 173, 2001: 1137–1146. The contents of this disclosure are hereby expressly incorporated herein by reference. The X-ray detector 5 is so dimensioned that the heart volume of a patient is possible without displacement in the direction of the system axis z.

The X-ray radiator 2 with the diaphragm 3 and the X-ray detector 5 with its radiation diaphragm 6, are attached to a gantry (not shown) opposite one another so that a pyramidal X-ray beam that emanates from the X-ray radiator 2 during operation of the CT device and is limited by the adjustable diaphragm 3, (the margin rays are referenced 8), strikes the X-ray detector 5. A cross-section of the X-ray beam is set by means of the diaphragm 3 and (if present) the beam diaphragm 6 such that only the region of the X-ray detector 5 that can be directly struck by the X-ray beam is irradiated. This consists of four rows of detector elements 4 designated as active rows in the operating mode represented in FIG. 1.

The gantry can be set into rotation around the system axis z by means of a drive device (not shown). The system axis z extends parallel to the z-axis of a rectangular spatial coordinate system represented in FIG. 1. The rotational angle is referenced φ.

The columns of X-ray detector 5 extend in the direction of the z-axis, whereas the rows, whose width b is measured in the direction of the z-axis and equals 1 mm, for example, extend perpendicular to the system axis z, i.e. the z-axis.

In order to be able to bring the subject, e.g. the patient, into the beam path of the X-ray beam, a support device 9 (patient table) is provided, which is displaceable parallel to the system axis z, i.e., in the direction of the z-axis.

The desired anatomical volume is scanned by means of the incremental displacement (sequence mode) of the support device 9 relative to the X-ray radiator 2 and the X-ray detector 5, or alternatively by means of a continuous table displacement (spiral scan).

In the sequence scan, measurement data are successively recorded from different slices which are respectively disposed perpendicular to the system axis z. There is no translational movement during the scanning of each of the slices with gantry rotation. A translation step is executed, however, for positioning the gantry in each new slice. In spiral mode, a desired value for the displacement h of the support 9 per gantry revolution is selected by means of a synchronization between the rotational movement of the gantry and the translational movement of the support device 9 in the sense of a constant (adjustable) ratio of translation speed to rotation speed. A volume of an examination subject who is located on the support device 9 is then examined, the volume scan taking the form of a spiral scan wherein a number of projections are acquired from different directions with each revolution of the gantry with the aid of gantry rotation and translation of the bearing device 9 occurring simultaneously. In the spiral scan, the focus F of the X-ray radiator 2 moves on a spiral path relative to the support device 9.

The measurement data corresponding to the individual projections, which are read in parallel fashion during the scan from the detector elements 4 of each active row of the detector system 5, undergo a digital/analog conversion in a data conditioning unit 10, whereupon they are serialized and sent to an image computer 11, which displays the result of an image reconstruction on a display unit 16, for instance a video monitor.

The X-ray radiator 2, for instance an X-ray tube, is supplied with the necessary voltages and currents by a generator unit 17 (which optionally co-rotates). In order to be able to set the required values, a control unit 18 with an input interface, specifically a keyboard 19, is allocated to the generator unit 17.

The remaining operation and control of the CT device 1 also are supervised by means of the control unit 18 and the keyboard 19, which is represented by the control unit 18 being connected to the image computer 11.

Among other things, the number of active rows of detector elements 4 and thus the position of the diaphragm 3 and the optional beam diaphragm 6 near the detector 5 can be adjusted, for which purpose the control unit 18 is connected to adjustment units 20 and 21 that are allocated to the diaphragm 3 and the optional beam diaphragm 6 near the detector 5, respectively. The rotation time required by the gantry for a complete rotation can also be set, which is represented by a drive unit 22 that is allocated to the gantry being connected to the control unit 18.

FIG. 2 shows a similar computed tomography apparatus 1 to that of FIG. 1, which is also suitable for implementing the inventive method. In this computed tomography apparatus 1, the control function are undertaken in the image computer, which is referenced 11. For simplicity, the drives of adjustment units 20, 21 and of drive unit 22 according to FIG. 1 have been omitted from FIG. 2. Instead, a drive unit 24 that is connected to the image computer 11 is represented, with which the subject (patient) 26 on the table of the support device 9 can be moved in the direction of the system axis z.

An exemplary embodiment of the inventive method is shown in FIG. 3. The method begins in the first step 31 with a linear scan (topogram) referred to as "z-scan". Here, transmission values are captured at different z-positions of the subject 26 without rotation of the X-ray radiator 2, for instance in a position such as that represented in FIG. 2. Transmission values are picked up at least from a large enough z region that a region that is to be examined is reliably covered, and therefore the linear scan data that are needed for a subsequent image reconstruction can be acquired by means of the first step 31 alone. In a second step 33, the result of the z scan is displayed, also gradually, on the display unit 16 (see FIG. 1 or 2).

With the input interface 19, the relevant region ROI (Region of Interest) can be selected from the display unit 16 by the operator by means of marking arrow 34 (FIG. 2).

In a third step 35, the topogram data T that are calculated from the linear scan in the first step 31 are stored in a topogram memory 37 (see FIG. 2) in the image computer 11.

After the successful selection of the relevant region ROI, a rotation scan (φ scan) occurs in a fourth step 39, wherein the X-ray radiator 2 makes several complete revolutions with a rotational angle φ between 0° and 360° at one or more constant z-positions. The examination of the patient occurs in the sequence mode, wherein scanning occurs at one or more different table positions while the gantry rotates. When a flat detector is used, it is possible to operate with a stationary patient table by the successive activation of different detectors by means of the beam diaphragm 6 at the detector 5.

The resulting raw dataset containing projection data is also stored in a fifth step 41. In a subsequent sixth step 43, the image reconstruction R takes place using both the topogram data and the projection data. A 3D image reconstruction is performed by means of a cone beam image reconstruction method. Approximative algorithms such as what is known as the Feldkamp algorithm or algorithms based thereon, as well as exact methods such as the aforementioned algorithms, can be used.

In a seventh step 45, the topogram or CT image is displayed on the display unit 16 as the result of the reconstruction step 43.

The inventive utilization of the initial data, which arise from both linear and rotational scans, for the image reconstruction guarantees that the scan in 3D Radon space is complete. Ideally, this space should contain all plane integrals of the beam cone of planes that are arbitrarily oriented in the examination subject.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for generating an image of an examination subject using a tomography-capable X-ray device having a multi-row X-ray detector array, an X-ray radiator rotatable around a system axis that emits a conical X-ray beam, and a positioning device adapted to receive an examination subject thereon for positioning the subject in a direction parallel to said system axis at different positions parallel to the system axis relative to the X-ray radiator, comprising the steps of:

generating raw data by radiating said examination subject with said X-ray beam in a rotation scan while successively moving said subject on said positioning device to respectively different positions in said direction parallel to said system axis to acquire a plurality of projections at each of said positions during at least one revolution of said X-ray radiator around the subject, and by generating a topogram with a linear scan wherein transmission values are acquired at different positions of said subject parallel to said system axis, without rotation of said X-ray radiator, with all of said transmission values generated by said linear scan being acquired in a continuous linear scanning movement; and generating an image of said subject from said raw data generated by said rotation scan and said topogram obtained by said linear scan.

2. A method for generating an image of an examination subject using a tomography-capable X-ray device having a multi-row X-ray detector array, an X-ray radiator rotatable around a system axis that emits a conical X-ray beam, and a positioning device adapted to receive an examination subject thereon for positioning the subject in a direction parallel to said system axis at different positions parallel to the system axis relative to the X-ray radiator, comprising the steps of:

acquiring a topogram of the subject by measuring transmission values of the subject at different positions of the subject along said direction parallel to the system axis, without rotation of said X-ray radiator;

displaying said topogram at a display unit and selecting a relevant region of the subject in the displayed topogram;

storing said topogram;

obtaining raw data of the examination subject in a rotation scan while successively moving said subject on said positioning device to respectively different positions in said direction parallel to said system axis by acquiring a plurality of projections of the subject at each of said positions during at least one revolution of the X-ray radiator around the subject; and reconstructing an image of the subject from the stored topogram in combination with the raw data acquired during the rotation scan.

3. A method as claimed in claim 2 comprising executing said rotation scan to cover at least said relevant region.

4. A method as claimed in claim 2 comprising acquiring all of the projections in said rotation scan in one continuous rotational movement of the X-ray radiator.

5. A method for generating an image of an examination subject using a tomography-capable X-ray device having a multi-row X-ray detector array, an X-ray radiator rotatable around a system axis that emits a conical X-ray beam, and a positioning device adapted to receive an examination subject thereon for positioning the subject in a direction parallel to said system axis at different positions parallel to the system axis relative to the X-ray radiator, comprising the steps of:

generating raw data by radiating said examination subject with said X-ray beam in a rotation scan, while successively moving said subject on said positioning device to respectively different positions in said direction parallel to said system axis, to acquire a plurality of projections at each of said positions during at least one rotation of said X-ray radiator around the subject, and by a linear scan wherein transmission values are acquired at different positions of said subject parallel to said system axis, without rotation of said X-ray radiator, with all of said transmission values generated by said linear scan being acquired in a continuous linear scanning movement; and generating an image of said subject from said raw data generated by said rotation scan and said linear scan.

6. A method as claimed in claim 5 comprising acquiring the transmission values during the continuous linear scanning movement in direct succession, with no intermediate rotation of said X-ray radiator.

7. A method as claimed in claim 5 comprising acquiring all of said projections by said rotation scan in one continuous rotational movement of the X-ray radiator.

8. A method as claimed in claim 5 comprising, in said rotational scan, acquiring a plurality of projections at a single position of said subject in said direction parallel to said system axis during at least one revolution of the X-ray radiator around the subject, and employing a flat detector as said multi-row X-ray detector array.

* * * * *